United States Patent [19]
Erlebacher et al.

[11] Patent Number: 5,350,399
[45] Date of Patent: Sep. 27, 1994

[54] PERCUTANEOUS ARTERIAL PUNCTURE SEAL DEVICE AND INSERTION TOOL THEREFORE

[76] Inventors: Jay Erlebacher, 55 Woodland Park Dr., Tenafly, N.J. 07670; Richard S. Goldweit, 82 Park St., Tenafly, N.J. 07670

[21] Appl. No.: 958,446

[22] Filed: Oct. 7, 1992

Related U.S. Application Data

[63] Continuation of Ser. No. 763,907, Sep. 23, 1991, abandoned.

[51] Int. Cl.⁵ .............................................. A61B 17/00
[52] U.S. Cl. ...................... 606/213; 606/151; 128/899
[58] Field of Search ............... 606/151, 213, 215, 232, 606/139; 604/15, 60, 285, 286, 288; 128/898, 899

[56] References Cited

U.S. PATENT DOCUMENTS

| | | | |
|---|---|---|---|
| 2,316,297 | 4/1943 | Southerland | 606/139 |
| 3,123,077 | 3/1964 | Alcamo | 606/228 |
| 3,956,504 | 5/1976 | Schneider | 514/567 |
| 4,007,743 | 2/1977 | Blake | 606/213 |
| 4,347,243 | 8/1982 | Schneider | 514/21 |
| 4,374,830 | 2/1983 | Schneider | 514/21 |
| 4,423,036 | 12/1983 | Schneider | 514/21 |
| 4,669,473 | 6/1987 | Richards et al. | 606/215 |
| 4,705,040 | 11/1987 | Mueller et al. | 606/108 |
| 4,744,364 | 5/1988 | Kensey | 606/213 |
| 4,796,612 | 1/1989 | Reese | 606/72 |
| 4,890,612 | 1/1990 | Kensey | 623/1 |
| 4,917,089 | 4/1990 | Sideris | 606/215 |
| 5,059,206 | 10/1991 | Winters | 606/213 |
| 5,089,008 | 2/1992 | Chen | 606/213 |

FOREIGN PATENT DOCUMENTS

| | | | |
|---|---|---|---|
| 0489252 | 10/1976 | Australia | 606/213 |
| 9014796 | 12/1990 | PCT Int'l Appl. | |

*Primary Examiner*—Stephen C. Pellegrino
*Attorney, Agent, or Firm*—Fulwider Patton Lee & Utecht

[57] ABSTRACT

The sealing device is composed of an intra-arterial occluder and an extra-arterial occluder, both made of resilient biocompatible and/or bioabsorbable material and held in place via a saw-toothed guide extending integrally from the intra-arterial occluder. An insertion tool is provided to effect sliding of the extra-arterial occluder over the guide and fixation of the extra-arterial occluder to the guide in sealed relation over an opening in body tissue and safe cutting of the guide. A force gauge is provided on the tool to indicate the sealing pressure on the intra-arterial occluder.

36 Claims, 2 Drawing Sheets

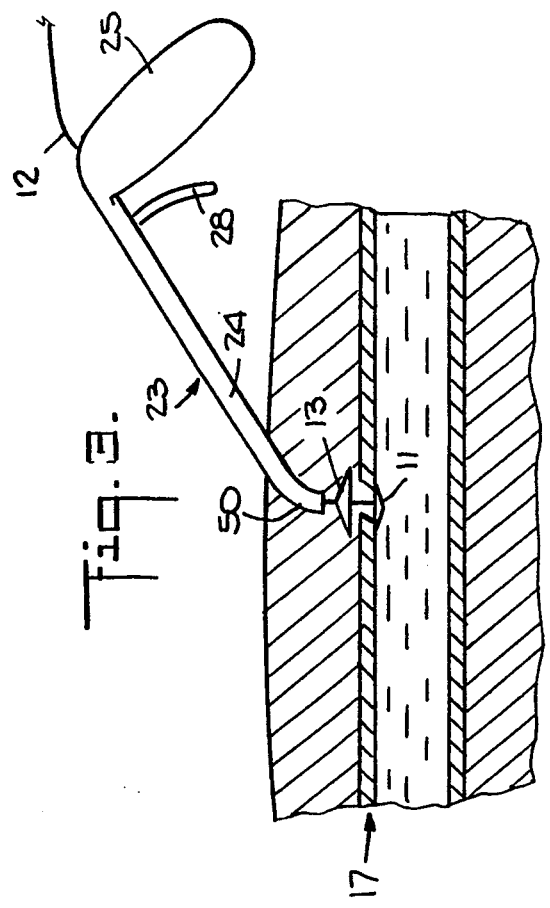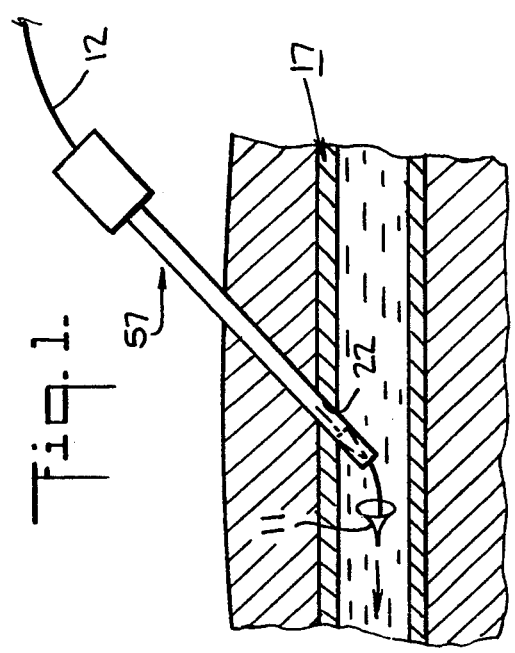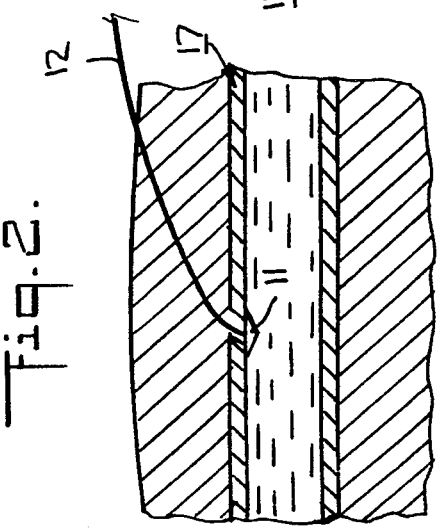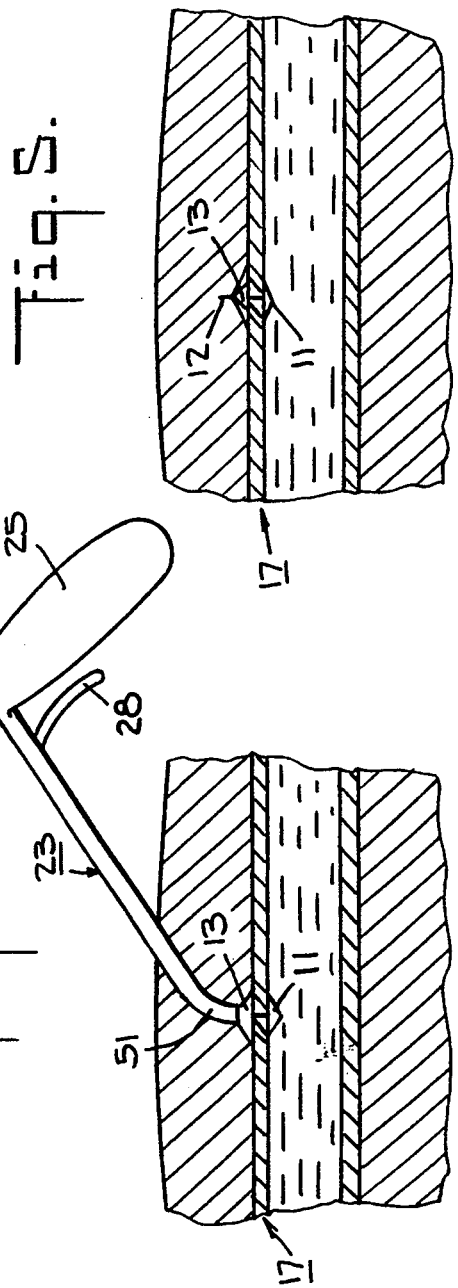

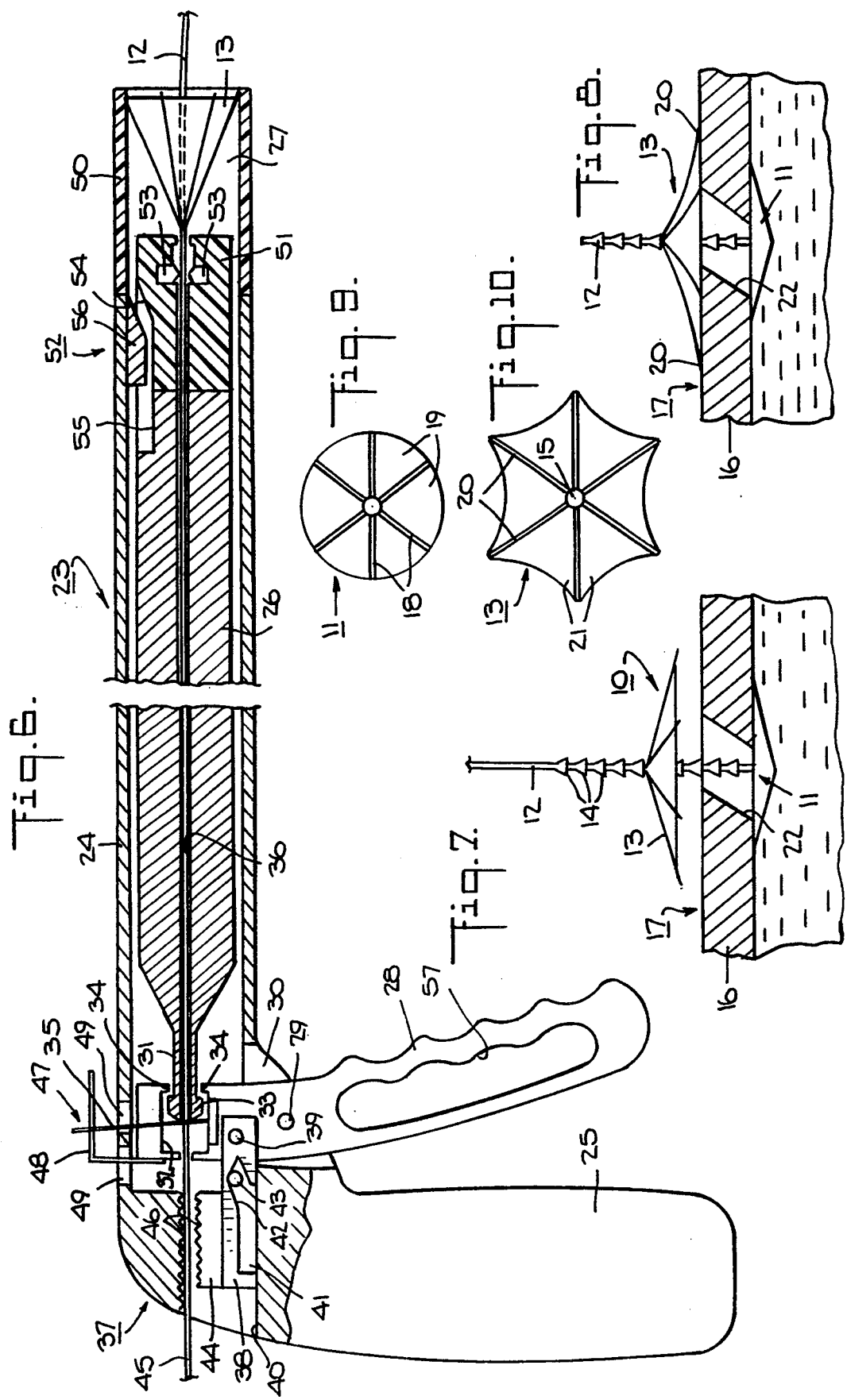

PERCUTANEOUS ARTERIAL PUNCTURE SEAL DEVICE AND INSERTION TOOL THEREFORE

This is a continuation of application Ser. No. 07/763,907, filed on Sep. 23, 1991, now abandoned.

This invention relates to a percutaneous arterial puncture seal device and an insertion tool therefore. More particularly, this invention relates to a sealing device for sealing an opening in a tissue and to a tool for implanting the device.

Heretofore, various interventional procedures have been performed which require formation of a puncture or the like in tissue and, for example, in a vessel for the introduction of various devices, such as catheters.

In particular, access to arterial and venous vascular systems is necessary for both diagnostic and therapeutic medical procedures.

For example, diagnostic arteriography is a radiologic procedure which permits visualization of the arterial system for the diagnosis of disease in various organ systems. The most frequent applications are cardiac catheterization, peripheral vascular angiography, mesenteric angiography, and cerebral angiography. Therapeutic trans-arterial procedures, such as percutaneous transluminal coronary angioplasty (PTCA), have expanded the use of arterial access even further.

All these techniques involve cannulation of an artery so that a catheter may be inserted and advanced into the arterial system. Radio-opaque dye can be injected through the catheter and into the arterial system being examined while X-ray images are recorded. Alternatively, various transcatheter therapies can be employed in the artery, using balloon dilation devices, atherectomy devices, lasers, intra-aortic counterpulsation devices and left ventricular assist devices.

The femoral artery at the junction of the thigh and the abdomen is the most frequent arterial puncture site, but the carotid artery in the neck, the brachial artery in the mid-arm, and the axillary artery are also used. A percutaneous sheath is usually used whenever multiple catheters are used.

When the sheath is removed, the 1.5 to 5.0 millimeter hole in the artery would spurt blood with significant blood loss unless certain measures are taken. To allow sealing of the hole with a solid clot, heavy pressure is applied to the groin, either manually or with a large C shaped clamp for 10 to 30 minutes. Afterwards, the patient must lie flat on his/her back for 6 to 8 hours, and is usually kept in the hospital overnight for observation. Movement at the hip joint and any increase in intra-abdominal pressure, such as with coughing or bowel movement can result in serious bleeding. There is a much greater tendency for serious bleeding to occur in patients given anticoagulants like aspirin and heparin or clot dissolving drugs like steptokinase or tissue plasminogen activator.

Over one million diagnostic and therapeutic arteriographic procedures are done annually in the U.S. The extra hospital days incurred purely to control bleeding from the arterial puncture site could be avoided if a safe, easy to use and effective arterial puncture sealant device were available. Such a device would allow same day discharge after angiographic procedures, with a savings of hundreds of millions of dollars. In addition to dollars saved, morbidity from bleeding and complications of blood transfusion could be virtually eliminated.

Various suggestions have also been made, such as described in U.S. Pat. Nos. 4,744,364; 4,852,568 and 4,890,612, for the mechanical sealing of such punctures. In such cases, a sealing device in the form of an expandable closure member is to be inserted through a puncture in the vessel, expanded while within the vessel and then retracted against and through the puncture by means of a retraction filament. Thereafter, the filament is left extending from the site of the puncture and through the skin of the patient while being secured in position on the skin of the patient as by a strip of conventional tape. However, such devices permit the exposed thread to be a site for infection. Further, anchorage of the enclosed member in place by a thread which passes through the skin of a patient may not be reliable so that bleeding may occur by accidental displacement of the sealant device. Further, displacement of the sealant device into the artery would result in arterial occlusion and gangrene.

Accordingly, it is an object of the invention to be able to reliably seal a puncture in a vessel or other tissue.

It is another object of the invention to provide a relatively simple sealing device for sealing punctures in an arterial vessel.

It is another object of the invention to provide a simple tool for implanting a percutaneous arterial sealing device in a patient.

It is another object of the invention to be able to safely seal punctures in vessels in a relatively easy and rapid reliable manner.

It is another object of the invention to reliably seal punctures with a measured pressure which will not damage the tissues within the seal.

It is another object of the invention to be able to deliver clot promoting drugs or materials to the outside of a blood vessel adjacent to a puncture wound.

Briefly, the invention provides a sealing device for sealing an opening in a vessel which is comprised of a first biocompatible member, such as a collapsible intra-arterial occluder, for positioning in a vessel to one side of an opening or puncture therein, a guide extending centrally from the member for passage through the opening in the vessel and a second biocompatible member, such as an extra-arterial occluder, which is movably mounted on the guide for positioning outside the vessel on an opposite side of the opening therein and in opposition to the first member in order to seal the opening.

The guide may be constructed in the form of a wire, for example of biocompatible material, integral with the intra-arterial occluder. Further, the guide may be provided with a plurality of teeth near a distal end so that the extra-arterial occluder can pass over the toothed portion in a direction towards the intra-arterial occluder while being retained against movement in the opposite direction.

The construction of the sealing device is such that each member is circumferentially collapsible while being resiliently expandable.

The extra-arterial occluder is constructed of larger outer dimensions than the intra-arterial occluder. Further, the intra-arterial and extra-arterial occluders can be made from biocompatible materials which have displayed their safety in humans, including but not limited to Dacron, Nylon, Gortex or Teflon. The guide could be made from wire, but other synthetic materials such as nylon would be applicable or even preferable.

Alternately, and probably preferably, biocompatible materials for the occluders and guide may be ideal, because they would slowly dissolve and leave no residual foreign material behind. Biocompatible materials should be chosen so that the rate of absorption of the various parts is differential. That is, the intra-arterial occluder and guide should absorb before the extra-arterial occluder to reduce the chance that the intra-arterial occluder could come free and embolize into the circulation.

Anti-thrombotic materials and/or drugs could be also used or incorporated into the blood contacting surface of the occluders. The occluders and guide may be radio-opaque so that they can be visualized fluoroscopically. Drugs or materials which promote coagulation could be used where the sealing surfaces exist.

The invention also provides a tool for the insertion of the sealing device in a patient. This tool includes a barrel, a handle at one end of the barrel, a positioner member slidably mounted in the barrel to define a chamber at one end of the barrel for receiving the extra-arterial occluder, and a trigger pivotally mounted on the handle and having one end disposed in the barrel. In addition, means are provided in the barrel between the end of the trigger and the positioner member for pushing the member in a direction out of the barrel in order to expel the extra-arterial occluder in response to pivoting of the trigger.

The positioner member is also hollow in order to define a bore for passage of the elongated guide which extends from the intra-arterial occluder. In addition, a clamp is provided in the handle for selectively clamping the guide passing therethrough in response to pivoting of the trigger and prior to movement of the positioner member.

The tool is also provided with a force gauge on the barrel for indicating the degree of pressure exerted via the clamped guide to the intra-arterial occluder during movement of the positioner member to expel the extra-arterial occluder from the tool.

The tool is also provided with a cutting means for severing the guide within the positioner member in response to retraction of the member into the barrel, for example a reverse pivoting of the trigger. This cutting means may include a pair of pincers in the positioning member disposed on opposite sides of the bore through which the guide passes as well as a cam surface on the positioning member and a cam on the barrel for slidably engaging the cam surface in order to radially deform the positioning member to effect closing of the pincers together to sever the guide therebetween.

The tool may also be constructed such that the positioner member and the barrel have flexible distal portions in order to facilitate securement of the extra-arterial occluder in place.

Basically, the insertion tool has several functions. First, the tool is to deploy the extra-arterial occluder into the tissues outside the arterial wall. Second, the tool is to provide for an application of a calibrated pressure to the intra-arterial occluder at the contact point of the occluder with the lumen of the vessel. Third, the tool functions so as to cut the guide upon completion of the positioning of the intra-arterial and extra-arterial occluders.

In use, the tool is initially provided in a sterile condition with the extra-arterial occluder contained within the chamber at the distal end of the barrel of the tool. At the conclusion of an arteriographic procedure, a percutaneous sheath would remain in the vessel, i.e., an artery. Thereafter, the intra-arterial occluder would be pushed through the sheath into the arterial lumen, for example, by an obturator whose length is only minimally greater than the sheath. In order to prevent arterial damage, the sheath is pulled back as the obturator is pushed in. As the intra-arterial occluder exits the sheath, the occluder expands due to the inherent natural resiliency to do so to normal full size. Once the occluder is in the artery, the position of the occluder can be confirmed by noting a free forward movement of the guide and resistance on pulling back. The sheath is then removed from the patient and the guide is pulled back until the intra-arterial occluder is snug against the luminal side of the arterial wall.

Thereafter, the tool is used to position the extra-arterial occluder. To this end, the guide is threaded through the extra-arterial occluder and tool. The tool is then manipulated to position the extra-arterial occluder outside the arterial wall, the appropriate position at which the extra-arterial occluder is to be deployed from the insertion tool into the patient can be determined by the location of a mark on the guide relative to the insertion tool. Alternatively, a stop can be placed on the guide which abuts the tool and prevents the tool tip from being inserted too close to the artery. At this position, the trigger on the tool is squeezed accomplishing several functions. First, the extra-arterial occluder is expelled from within the barrel. At this time, the extra-arterial occluder expands radially under the natural resiliency of the occluder. In this respect, the extra-arterial occluder may have a web-like perimeter from which struts project to positively engage the tissues as the extra-arterial occluder exits from the insertion tool, encouraging the extra-arterial occluder to open as intended.

Second, the two occluders are pressed together with a pressure regulated by the operator and measured by the tool. Further, since the distal end of the tool is flexible, the distal end is able to conform to a position substantially perpendicular to the artery as the occluders are pressed together.

By making the extra-arterial occluder larger than the intra-arterial occluder, several advantages are obtained. First, the larger size insures that the extra-arterial occluder cannot accidentally be inserted into the artery. Second, the force applied to hold the two occluders together will be applied to a larger surface area, thus reducing the pressure on the tissues. Thus, an excessively high pressure which could result in death of the underlying tissue (necrosis) is avoided.

Once the occluders are properly seated, the cutting means within the tool can be activated to sever the guide just after the point of exit from the extra-arterial occluder. The tool can then be withdrawn leaving the artery positively sealed. In this case, no part of the sealing device remains external to the patient. Instead, the entire sealing device is implanted within the tissue which heals around the device.

These and other objects and advantages of the invention will become more apparent form the following description taken in conjunction with the accompanying drawings wherein:

FIG. 1 illustrates a view at the conclusion of an arteriographic procedure with a sheath in place and an intra-arterial occluder inserted within an arterial vessel in accordance with the invention:

FIG. 2 illustrates a view similar to FIG. 1 with the intra-arterial occluder of the sealing device in place against the wall of the vessel;

FIG. 3 illustrates a view similar to FIGS. 1 and 2 with an insertion tool constructed in accordance with the invention in place coaxially surrounding the guide extending from the intra-arterial occluder through the insertion tool;

FIG. 4 illustrates a view similar to FIG. 3 of the tool at a time at which the extra-arterial occluder is being secured to the guide extending from the intra-arterial occluder;

FIG. 5 illustrates a cross sectional view of an arterial vessel with a sealing device according to the invention in place;

FIG. 6 illustrates a part cross sectional view of the insertion tool of FIG. 3 as constructed in accordance with the invention;

FIG. 7 illustrates a enlarged view of a sealing device in accordance with the invention;

FIG. 8 illustrates a view of the sealing device of FIG. 7 in fixed position over an opening in an arterial vessel in accordance with the invention;

FIG. 9 illustrates a plan view of the intra-arterial occluder constructed in accordance with the invention; and FIG. 10 illustrates a plan view of the extra-arterial occluder constructed in accordance with the invention.

Referring to FIG. 7 and FIG. 8, the sealing device 10 is constructed of a biocompatible and/or bioabsorbable member in the form of an intra-arterial occluder 11, a guide means in the form of an elongated biocompatible and/or bioabsorbable wire 12 integral with and extending centrally from the intra-arterial occluder 11 and a second biocompatible and/or bioabsorbable member in the form of an extra-arterial occluder 13. As indicated, the guide 12 includes a portion extending from the intra-arterial occluder 11 which contains a plurality of saw teeth 14 while the extra-arterial occluder 13 is provided with an opening 15 (see FIG. 10) through which the guide 12 passes. The saw teeth 14 are wider in diameter than the opening 15 in the extra-arterial occluder 13 so that the extra-arterial occluder 13 can be passed over the teeth 14 in a direction towards the intra-arterial occluder 11. Thus, the extra-arterial occluder 13 can be advanced until a desired amount of pressure is placed on the tissues, such as the wall 16 of an artery 17, while being retained against movement in an opposite direction.

Each occluder 11, 13 is formed of a material and a shape so as to be circumferentially collapsible, for example from the normal position shown in FIGS. 9 and 10. Further, each occluder 11, 13 is made to be resiliently expandable from a collapsed state into the normal positions as shown in FIGS. 9 and 10.

As shown in FIG. 9, the intra-arterial occluder 11 is of circular disc shape and is provided with a plurality of radial struts 18 integral with flexible sections 19 therebetween.

As shown in FIG. 10, the extra-arterial occluder 13 is of umbrella-like construction having a plurality of radially disposed struts 20 with integral web-like sections 21 therebetween. Further, the struts 20 extend radially outwardly of the web portions 21 so as to engage the tissue outside of the vessel 17 (see FIG. 7) to encourage circumferential opening of the occluder 13.

As indicated in FIGS. 9 and 10, the extra-arterial 13 is of larger outer dimensions than the intra-arterial occluder 11.

Both occluders 11, 13 are made of a suitable biocompatible material which may as well be a bioabsorbable material so as to be absorbed over time. In this respect, the rate of absorption of the intra-arterial occluder 11 is faster than that of the extra-arterial occluder 13 and the guide 12 to reduce the risk of the intra-arterial occluder 11 coming free.

Referring to FIGS. 7 and 8, the sealing device 10 is constructed such that the intra-arterial occluder 11 can be placed on the inside of the vessel 17 over an opening or puncture 22 therein while the extra-arterial occluder 13 is secured over the outside of the vessel 17 on the opposite side of the opening 22. The degree of pressure between the occluders 11, 13 should be sufficient to seal the opening 22 while at the same time not creating undue pressure on the wall 16 of the vessel 17.

Referring to FIG. 6, the insertion tool 23 is constructed so as to facilitate implantation of the sealing device 10. As illustrated, the tool 23 includes a barrel 24, a handle 25 which is fixed to one end of the barrel 24, a positioner member 26 which is slidably mounted in the barrel 24 to define a chamber 27 at one end for receiving the extra-arterial occluder 13 and a trigger 28 which is pivotally mounted on the handle 25 with one end disposed in the barrel 24. As indicated, the trigger 28 is mounted via a pivot pin 29 which is fixed within a yoke 30 integral with the handle 25.

In addition, a stem or extension 31 extends from the positioner 26 into a recess 32 in one end of the trigger 28 and is provided with an enlarged head 33 within the recess 32. As illustrated, the entrance to the recess 32 is formed by a pair of projections 34 which serve to define a slot through which the extension 31 may pass while preventing outward passage of the enlarged head 33. For purposes of assembly, the projections 34 may be sufficiently flexible to permit introduction of the head 33 or may be formed as separate pieces which are removably secured to the trigger 28 in a suitable fashion to permit assembly of the head 33 within the recess 32.

The extension 31 and head 32 serve as a means for pushing the positioner member 26 in a direction out of the barrel 24 in order to expel the extra-arterial occluder 13 therefrom.

A spring wire 35 is also mounted in the trigger 28 to extend through the recess 32 and upwardly, as viewed, through an appropriate slot in the barrel 24 for purposes as described below. The spring wire 35 abuts against the head 33 on the stem 31 so as to transfer a pushing force on the head 33 and thus the positioner member 26 so as to push the member 26 in a direction out of the barrel 24 in order to expel the extra-arterial occluder 13 therefrom.

The positioner member 26 is hollow so as to define a through bore 36 for passage of the guide 12 therethrough. In addition, a clamp 37 is provided within the handle 25 for selectively clamping the guide 12 passing therethrough in response to pivoting of the trigger 28 and prior to movement of the positioner member 26. As indicated, a means is provided between the trigger 28 and the clamp 37 in order to effect a clamping action. This means includes a guide clamp actuator 38 which is pivotally mounted at one end on a pivot pin 39 secured to the trigger 28. In addition, the actuator 38 is slidably mounted within a recess 40 of the handle 25 and has a recess 41 which contains a cam surface 42 which rides on a fixed pin 43 in the handle 25. In addition, the actuator 38 carries one jaw 44 of the clamp 37 in facing relation to a second jaw 45 of the clamp 37 which is integral with the handle 25. As indicated, each jaw 44, 45 has a plurality of serrations 46 to grip the guide 12.

Upon pivoting of the trigger 28 in a clockwise direction, as viewed, the actuator 38 is slid to the right relative to the jaw 44 and raised via the pin 43 thereby bringing the jaws 44, 45 together about the guide 12.

The tool 23 is also provided with a force gauge 47 on the barrel 24 for indicating a degree of pressure exerted on the clamped guide 12 during movement of the positioner member 26 relative to the guide 12. This force gauge 47 is calibrated in pressure units of millimeters of mercury to reflect the force applied to the surface area of the intra-arterial occluder 11 (see FIG. 7). It is expected that the pressure applied by the operator will be between diastolic and just above systolic blood pressure although the optimal pressure necessary should be determined from clinical trials.

The force gauge 47 is constructed as an L-shaped element which is mounted on the end of the trigger 28 and which projects through a slot in the barrel 24. In addition, the exposed leg 48 of the gauge 47 carries a printed calibrated scale (not shown) which is coordinated with the spring wire 35 so as to provide a read out of the force applied to the spring wire 35 during pivoting of the trigger 28 in a clockwise manner as viewed. As indicated in FIG. 6, a pair of slots 49 may be provided in the barrel 24, one for the spring wire 35 and one for the gauge 47.

As shown in FIG. 6, the distal end of the barrel 24 is provided with a flexible tip 50 while the positioner member 26 is provided with a flexible tip 51. This permits the tool 27 to bend at the end when the extra-arterial occluder 13 is being implanted.

By way of example, the flexible tip 50 of the barrel 24 may be effected by parallel slots which are cut into the barrel 24 from opposite sides without reaching the midline of the barrel 24. This allows the barrel to bend in a plane parallel to the handle 25 of the tool 23. In like manner, the flexible tip 51 of the positioner member 26 may be formed with slots of the same nature. In addition, the surface of the barrel 24 and the positioner member 26 can be lined with a flexible and deformable material which will allow them to slide past each other without undue resistance.

In addition, a cutting means 52 is provided for severing the guide 12 within the positioner member 26 in response to retraction of the member 26 into the barrel 24 after implanting of the extra-arterial occluder 13. As indicated, this cutting means 52 includes a pair of pincers 53 in the flexible positioner tip 51 on opposite sides of the bore 36, a cam surface 54 within a groove 55 of the positioner 26 and a cam 56 fixedly mounted on the inside wall of the barrel 24 for slidably engaging the cam surface 54 in order to radially deform the flexible positioner tip 51 so as to effect closing of the pincers 53 together to sever the guide 12 therebetween.

Referring to FIG. 1, in order to seal the opening 22 in the artery 17, for example at the end of an arteriographic procedure, a percutaneous sheath 57 which is normally used in that procedure is retained in place. The intra-arterial occluder 11 which when deployed is larger than the anticipated opening 22, together with the guide 12 is pushed through the sheath 57 into the lumen of the artery 17 by an obturator (not shown). As the occluder 11 exits the sheath 57, the occluder 11 resiliently expands to full size.

Next, referring to FIG. 2, the intra-arterial occluder 11 is pulled back against the inside wall of the artery 17 and the sheath 57 removed.

Next, the insertion tool 23 is slid over the guide 12. At this time, the collapsed extra-arterial occluder 13 nests in the chamber 27 (see FIG. 6) of the tool 23 while the guide 12 passes through the extra-arterial occluder 13 and through the entire tool 23.

When the trigger 28 on the tool 23 is activated, two sequential functions occur, one after the other. First, the guide 12 is clamped in place relative to the tool 23 via the clamp 37. In this respect, during initial travel, the trigger 28 moves the clamp actuator 38 forwardly, i.e., to the right as shown in FIG. 6. The actuator 38 then translates upwardly to force the clamp jaws 44, 45 (or other high friction mechanism) together in order to fix the guide 12 in place. During this part of the trigger movement, there is no movement of the positioner member 26.

Next, as the trigger 28 continues to pivot, the end of the trigger 28 pushes the spring wire 35 in contact with the enlarged head 33 and, thus, the positioner member 26. The spring wire 35 then deforms toward the rear of the tool in proportion to the force applied as the positioner member 26 moves forwardly to expel the extra-arterial occluder 13 (FIG. 3). The force which is applied to the positioner member 26 is resisted by the guide 12 which is fixed in place by the guide clamp 37. The resisting force is transmitted through the guide 12 to the intra-arterial occluder 11 which is being pressed against the inner surface of the arterial wall. The force applied divided by the known surface area of the intra-arterial occluder 11 yields the pressure exerted against the wall of the artery by the intra-arterial occluder. This pressure is registered on the calibrated scale printed on the force/pressure gauge 47.

As the travel of the trigger 28 continues, the extra-arterial occluder 13 is advanced along the guide 12 until exiting the tool 23. Thereafter, an increase in spreading force is applied between the extra-arterial occluder 13 and the fixed guide 12 (See FIG. 4). The force on the guide 12 and the positioner member 26 which is registered on the force gauge 47 is effectively transmitted to the intra-arterial occluder 11. As pressure is applied, the flexible tip 50 of the barrel 24 and the flexible tip 51 of the positioner member 26 conform to a shape perpendicular to the wall 16 of the vessel 17 (see FIG. 4).

Once the extra-arterial occluder 13 is positioned, the guide 12 is severed. To this end, the trigger 28 is pivoted in a reverse direction, i.e. counterclockwise as viewed in FIG. 6, so as to retract the positioner member 26 into the barrel 24. To this end, the trigger 28 is provided with a cut-out 57 to accommodate the fingers so that the trigger 28 is easily pulled away from the handle 25.

As the positioner member 26 retracts, the cam 56 engages the cam surface 54 of the flexible positioner tip 51 causing the pincers 53 to come together. The pincers 53 then exert a sufficient force to sever the guide 12 thereat. Since the cutting operation occurs within the positioner member 26, there is little danger of cutting the guide 12 too short which could inadvertently allow the intra-arterial and extra-arterial occluders 11, 13 to separate.

The insertion tool 23 is then removed from the patient and a band-aid or similar dressing is applied to the wound.

Of note, the occluders 11, 13 may be held together at the desired pressure other then through the use of the guide saw teeth 46. For example, glues may be used.

The invention thus provides a sealing device which is fixedly secured in place completely internal in the patient. There are no external members which may leave a path for infection into the patient. Further, the sealing device may be used to close percutaneous punctures in any number of body parts including, but not limited to, the gall bladder, stomach, intestine, lung, heart, urinary bladder, urinary collecting systems and veins.

Further, the invention provides a tool which can be readily manipulated to implant a sealing device totally within a patient.

Further, the invention provides a relatively simple tool for the deployment of a sealing device about an opening in body tissues.

Still further, the invention provides a tool which is capable of measuring the occluder pressure during insertion.

What is claimed is:

1. A sealing device for sealing an opening in a vessel comprising
   a first resiliently expandable member for positioning in a vessel to one side of an opening therein for closing over said opening;
   a guide means integral with and extending centrally from said member for passage through the opening in the vessel, said guide including a portion containing a plurality of saw teeth; and
   a second resiliently expandable member movably mounted on said guide means for positioning outside the vessel on an opposite side of the opening therein and in opposition to said first member to seal the opening, said second member being slidably mounted on said guide means to pass over said portion in a direction towards said first member and to be retained against movement in an opposite direction by said saw teeth.

2. A sealing device as set forth in claim 1 wherein each said member is made one of a biocompatible material and a bioabsorbable material.

3. A sealing device as set forth in claim 2 wherein said members and said guide means are made of bioabsorbable material and said first member has a faster rate of absorption than said second member and said guide means.

4. A sealing device as set forth in claim 1 wherein at least one of said members has at least one of an anti-thrombotic material and a clot-promoting material therein.

5. A sealing device as set forth in claim 1 wherein said guide means is an elongated flexible wire.

6. A sealing device as set forth in claim 1 wherein said first member is resiliently expandable into a circular disc shape and said second member is resiliently expandable into an umbrella shape.

7. A sealing device as set forth in claim 6 wherein said second member is of larger outer dimensions than said first member.

8. A sealing device comprising
   a collapsible intra-arterial occluder for positioning in a vessel to one side of an opening therein;
   a guide wire non-removably connected to said occluder, said wire being integral with and extending centrally from said occluder for passage through the opening in the vessel;
   a collapsible extra-arterial occluder movably mounted on said guide wire for positioning on an opposite side of the opening in the vessel; and
   means between said extra-arterial occluder and said guide wire for fixing said extra-arterial occluder directly to said guide wire opposite said intra-arterial occluder to seal the opening in the vessel.

9. A sealing device as set forth in claim 8 wherein said extra-arterial occluder is resiliently expandable into an umbrella shape.

10. A sealing device as set forth in claim 9 wherein said intra-arterial occluder is resiliently expandable from a collapsed state into a circular disc shape.

11. A sealing device as set forth in claim 8 wherein said guide wire includes a portion containing a row of saw teeth and said extra-arterial occluder is slidably mounted on said guide wire to pass over said portion in a direction towards said intra-arterial occluder and to be retained against movement in an opposite direction.

12. A sealing device as set forth in claim 8 wherein each occluder and guide is bioabsorbable.

13. A sealing device comprising
   a collapsible intra-arterial occluder for positioning in a vessel to one side of an opening therein;
   a guide means extending centrally from said occluder for passage through the opening in the vessel and including a portion containing a row of saw teeth; and
   an extra-arterial occluder movably mounted on said guide for positioning on an opposite side of the opening in the vessel, said extra-arterial occluder being slidably mounted on said guide means to pass over said portion in a direction towards said intra-arterial occluder and to be retained against movement in an opposite direction.

14. A sealing device comprising
   a collapsible intra-arterial occluder of bioabsorbable material for positioning in a vessel to one side of an opening therein;
   a guide means of bioabsorbable material extending centrally from said occluder for passage through the opening in the vessel; and
   an extra-arterial occluder of bioabsorbable material movably mounted on said guide means for positioning on an opposite side of the opening in the vessel.

15. A sealing device for sealing an opening in a vessel comprising
   a first circumferentially collapsible bioabsorbable member for positioning in a vessel to one side of an opening therein;
   a guide means with and extending centrally from said member for passage through the opening in the vessel; and
   a second circumferentially collapsible member movably mounted on said guide for positioning outside a vessel on an opposite side of an opening therein and in opposition to said first member to seal the opening.

16. A sealing device as set forth in claim 15 wherein said second member has a plurality of radially disposed struts for engaging tissue outside of the vessel to encourage circumferential opening of said second member.

17. A sealing device for sealing an opening in a vessel comprising
   a first member made of at least one of a biocompatible material and a bioabsorbable material for positioning inn a vessel to one side of an opening therein for closing over the opening;

a guide means integral with and extending centrally from said member for passage through the opening in the vessel, said guide including a portion containing a plurality of saw teeth; and a second member made of at least one of a biocompatible material and a bioabsorbable material movably mounted on said guide means for positioning outside a vessel on an opposite side of an opening therein and in opposition to said first member to seal the opening, said second member having a slower rate of absorption than said second member and said guide means, said first member being slidably mounted on said guide means to pass over said portion in a direction towards said first member and to be retained against movement in an opposite direction by said saw teeth.

18. A sealing device for sealing an opening in a vessel comprising a first member of bioabsorbable material for positioning in a vessel to one side of an opening therein;

a guide means of bioabsorbable material extending centrally from said member for passage through the opening in the vessel; and a second member of bioabsorbable material mounted on said guide means for positioning outside the vessel on an opposite side of the opening therein an din opposition to said first member to seal the opening, said second member having a slower rate of absorption than said first member.

19. In combination, a first occluder for positioning in a vessel to one side of an opening therein;

a guide extending from said occluder;

a tool having a barrel;

a positioner member slidably mounted in said barrel to define a chamber at one end thereof, said member having a bore extending longitudinally therethrough and having said guide extending therethrough;

a clamp for clamping said guide relative to said barrel;

means for moving said positioner member in a direction out of said barrel; and a second occluder received in said chamber of said barrel in slidably mounted relation on said guide for movement along said guide in response to movement of said member in said barrel.

20. The combination as set forth in claim 19 wherein said tool includes a force gauge on said barrel for indicating a degree of pressure exerted via said clamp guide to said first occluder during movement of said positioner member relative thereto.

21. The combination as set forth in claim 19 wherein said tool includes a cutting means on said positioner member for severing the guide within said positioner member in response to retraction of said member into said barrel.

22. The combination as set forth in claim 19 wherein said tool includes a handle having said barrel mounted thereon, and a trigger pivotally mounted on said handle with one end within said barrel for actuating said means to push said positioner member relative to said barrel.

23. The combination as set forth in claim 22 which further comprises means articulated between said trigger and said clamp for actuating said clamp in response to pivoting of said trigger to clamp said guide therein.

24. The combination as set forth in claim 22 wherein said trigger has a recess at one end and said means for moving includes an extension on said positioner member having an enlarged head received in said recess.

25. A seal insertion tool comprising a barrel;

a positioner member slidably mounted in said barrel to define a chamber at one end of said barrel for receiving an extra-arterial occluder therein, said member being hollow to define a bore for passage of an elongated guide therethrough;

a handle at one end of said barrel;

a trigger pivotally mounted on said handle and having one end disposed in said barrel;

means in said barrel between said one end of said trigger and said positioner member for pushing said member in a direction out of said barrel in response to pivoting of said one end of said trigger towards said member to expel an extra-arterial occluder therefrom; and a clamp in said handle for passage of the elongated guide therethrough and for selectively clamping the elongated guide in response to pivoting of said trigger and prior to movement of said positioner member in said barrel.

26. A tool as set forth in claim 25 which further comprises a force gauge on said barrel for indicating a degree of pressure exerted via said clamped guide onto an intra arterial occluder positioned on one side of a puncture during movement of said positioner member relative thereto.

27. A tool as set forth in claim 25 which further comprises a cutting means for severing the guide within said positioner member in response to retraction of said member into said barrel.

28. A tool as set forth in claim 27 wherein said cutting means includes a pair of pincers in said positioner member disposed on opposite sides of said bore, a cam surface on said member and a cam on said barrel for slidably engaging said cam surface to radially deform said member to effect closing of said pincers together to sever the guide therebetween.

29. A tool as set forth in claim 28 wherein said member has a flexible distal portion containing said pincers therein.

30. A tool as set forth in claim 25 wherein said trigger has a recess at said one end and said means for pushing includes an extension on said positioner member having an enlarged head received in said recess.

31. A tool for inserting an arterial wound puncture seal device, said tool comprising a barrel;

a positioner member slidably mounted in said barrel to define a chamber at one end of said barrel for receiving an extra-arterial occluder having a bore therein, said member defining a bore for passage of an elongated guide extending from an intra-arterial occluder positioned on one side of the puncture;

means for pushing said member in a direction out of said barrel to expel the extra-arterial occluder along the elongated guide passing therethrough to a position on an opposite side of the puncture from the intra-arterial occluder;

a clamp for selectively clamping the guide passing therethrough prior to movement of said positioner member relative to said barrel; and a force gauge for indicating a degree of pressure exerted on a clamped guide during movement of said positioner member relative to the guide on said barrel.

32. A tool as set forth in claim 31 which further comprises a cutting means for severing the guide within said positioner member after implantation of the extra-arterial occluder.

33. A tool for inserting an arterial wound puncture seal device, said tool comprising a barrel;

a positioner member slidably mounted in said barrel to define a chamber at one end of said barrel for receiving an extra-arterial occluder having a bore therein, said member defining a bore for passage of an elongated guide extending from an intra-arterial occluder positioned on one side of a puncture;

means for pushing said member in a direction out of said barrel to expel the extra-arterial occluder along the elongated guide passing therethrough to a position on an opposite side of the puncture from the intra-arterial occluder; and a cutting means for severing the guide on said positioner member after implantation of the extra-arterial occluder.

34. A seal insertion tool for sealing a puncture comprising a barrel for receiving an elongated guide extending from a first occluder disposed on one side of a puncture and with said guide passing through the puncture;

a positioner member slidably mounted in said barrel for abutting a second occluder thereat, said member being hollow to define a bore for passage of the guide therethrough;

a handle at one end of said barrel;

a trigger pivotally mounted on said handle and having one end disposed in said barrel;

means in said barrel between said one end of said trigger and said positioner member for pushing said member in a direction out of said barrel and along the elongated guide in response to pivoting of said one end of said trigger towards said member to expel the second occluder therefrom;

a clamp in said handle for passage of the elongated guide therethrough and for selectively clamping the elongated guide in response to pivoting of said trigger and prior to movement of said positioner member in said barrel; and a force gauge for indicating a degree of pressure exerted via said clamped guide onto the first occluder during movement of said positioner member relative thereto.

35. A tool as set forth in claim 34 which further comprises a cutting means for severing the guide within said positioner member in response to retraction of said member into said barrel.

36. A method of sealing an arterial wound puncture comprising the steps of passing a resiliently expandable intra-arterial occluder through a percutaneous sheath into a lumen of an artery, said occluder having an elongated guide extending therefrom;

removing the sheath from the artery;

pulling the occluder against an inside wall of the artery over a puncture therein;

passing the elongated guide through an extra-arterial occluder nested in a chamber of an insertion tool and through a barrel of the tool while sliding the tool over the guide to position the tool opposite the artery;

thereafter clamping the guide within the tool;

thereafter expelling the extra-arterial occluder from the tube and along the guide to position the extra-arterial occluder outside the artery on a side of the puncture opposite the intra-arterial occluder; and thereafter severing the guide within the tool at a point spaced from the extra-arterial occluder.

* * * * *